US009474522B2

(12) United States Patent
Deck et al.

(10) Patent No.: US 9,474,522 B2
(45) Date of Patent: Oct. 25, 2016

(54) JAWED RECEIVER FOR NEEDLE CARTRIDGE

(71) Applicant: Ethicon Endo-Surgery, Inc., Cincinnati, OH (US)

(72) Inventors: Andrew C. Deck, Dayton, OH (US); Daniel J. Mumaw, Liberty Township, OH (US); David T. Martin, Milford, OH (US); Daniel L. Geiger, Newport, KY (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 245 days.

(21) Appl. No.: 14/297,993

(22) Filed: Jun. 6, 2014

(65) Prior Publication Data

US 2015/0351744 A1 Dec. 10, 2015

(51) Int. Cl.
*A61B 17/04* (2006.01)
*A61B 17/29* (2006.01)
*A61B 17/00* (2006.01)
*A61B 17/06* (2006.01)

(52) U.S. Cl.
CPC .......... *A61B 17/0469* (2013.01); *A61B 17/29* (2013.01); *A61B 2017/00407* (2013.01); *A61B 2017/00473* (2013.01); *A61B 2017/0608* (2013.01); *A61B 2017/2927* (2013.01); *A61B 2017/2929* (2013.01); *A61B 2017/2936* (2013.01); *A61B 2217/007* (2013.01)

(58) Field of Classification Search
CPC .............. A61B 17/06061; A61B 2017/00407; A61B 17/0625; A61B 17/0469; A61B 17/06114
See application file for complete search history.

(56) References Cited

U.S. PATENT DOCUMENTS

| 1,579,379 | A | 4/1926 | Marbel |
|---|---|---|---|
| 1,822,330 | A | 9/1931 | Ainslie |
| 1,884,149 | A | 10/1932 | Nullmeyer |
| 2,291,181 | A | 7/1942 | Alderman |
| 3,168,097 | A | 2/1965 | Dormia |
| 3,598,281 | A | 8/1971 | Watermeier |

(Continued)

FOREIGN PATENT DOCUMENTS

| DE | 4310315 A1 | 10/1993 |
|---|---|---|
| EP | 0674875 A1 | 10/1995 |

(Continued)

OTHER PUBLICATIONS

U.S. Appl. No. 13/832,595, filed Mar. 15, 2013 by Ethicon Endo-Surgery, Inc.

(Continued)

*Primary Examiner* — Gregory Anderson
*Assistant Examiner* — Christina Lauer

(57) ABSTRACT

A surgical suturing device comprises a cartridge having a needle and suture. An elongate shaft has a proximal end and a distal end. An actuator is connected to the proximal end of the elongate shaft. A pair of jaws is connected to the distal end of the elongate shaft. The jaws have a closed position adapted to receive and retain the cartridge, and wherein the jaws are latched in the closed position. The jaws also have a partially opened position adapted to release the cartridge wherein the jaws are biased by a spring from the first opened position towards the closed position. The jaws also have and a fully opened position spaced apart further than the partially opened position, wherein spring does not bias the jaws towards the closed position.

13 Claims, 13 Drawing Sheets

(56) References Cited

U.S. PATENT DOCUMENTS

| | | |
|---|---|---|
| 3,749,238 A | 7/1973 | Taylor |
| 4,027,608 A | 6/1977 | Arbuckle |
| 4,123,982 A | 11/1978 | Bess, Jr. et al. |
| 4,196,836 A | 4/1980 | Becht |
| 4,235,177 A | 11/1980 | Arbuckle |
| 4,406,237 A | 9/1983 | Eguchi et al. |
| 4,417,532 A | 11/1983 | Yasukata |
| 4,440,171 A | 4/1984 | Nomoto et al. |
| 4,557,265 A | 12/1985 | Andersson |
| 4,899,746 A | 2/1990 | Brunk |
| 5,209,747 A | 5/1993 | Knoepfler |
| 5,282,806 A | 2/1994 | Haber et al. |
| 5,289,963 A | 3/1994 | McGarry et al. |
| 5,306,281 A | 4/1994 | Beurrier |
| 5,308,353 A | 5/1994 | Beurrier |
| 5,312,023 A | 5/1994 | Green et al. |
| 5,318,578 A | 6/1994 | Hasson |
| 5,383,888 A | 1/1995 | Zvenyatsky et al. |
| 5,389,103 A | 2/1995 | Melzer et al. |
| 5,403,347 A | 4/1995 | Roby et al. |
| 5,403,354 A | 4/1995 | Adams et al. |
| 5,437,681 A | 8/1995 | Meade et al. |
| 5,454,823 A | 10/1995 | Richardson et al. |
| 5,470,338 A | 11/1995 | Whitfield et al. |
| 5,478,344 A | 12/1995 | Stone et al. |
| 5,478,345 A | 12/1995 | Stone et al. |
| 5,480,406 A | 1/1996 | Nolan et al. |
| 5,527,321 A | 6/1996 | Hinchliffe |
| 5,540,704 A | 7/1996 | Gordon et al. |
| 5,540,705 A | 7/1996 | Meade et al. |
| 5,540,706 A | 7/1996 | Aust et al. |
| 5,553,477 A | 9/1996 | Eisensmith et al. |
| 5,554,170 A | 9/1996 | Roby et al. |
| 5,560,532 A | 10/1996 | DeFonzo et al. |
| 5,569,301 A | 10/1996 | Granger et al. |
| 5,571,090 A | 11/1996 | Sherts |
| 5,591,181 A | 1/1997 | Stone et al. |
| 5,593,421 A | 1/1997 | Bauer |
| 5,610,653 A | 3/1997 | Abecassis |
| 5,617,952 A | 4/1997 | Kranendonk |
| 5,630,825 A | 5/1997 | de la Torre et al. |
| 5,632,746 A | 5/1997 | Middleman et al. |
| 5,643,295 A | 7/1997 | Yoon |
| 5,645,552 A | 7/1997 | Sherts |
| 5,649,961 A | 7/1997 | McGregor et al. |
| 5,665,096 A | 9/1997 | Yoon |
| 5,665,109 A | 9/1997 | Yoon |
| 5,669,490 A | 9/1997 | Colligan et al. |
| 5,674,229 A | 10/1997 | Tovey et al. |
| 5,674,230 A | 10/1997 | Tovey et al. |
| 5,693,071 A | 12/1997 | Gorecki et al. |
| 5,702,408 A | 12/1997 | Wales et al. |
| 5,707,379 A | 1/1998 | Fleenor et al. |
| 5,709,693 A | 1/1998 | Taylor |
| 5,713,910 A | 2/1998 | Gordon et al. |
| 5,728,107 A | 3/1998 | Zlock et al. |
| 5,728,108 A | 3/1998 | Griffiths et al. |
| 5,733,293 A | 3/1998 | Scirica et al. |
| 5,741,277 A | 4/1998 | Gordon et al. |
| 5,755,729 A | 5/1998 | de la Torre et al. |
| 5,759,188 A | 6/1998 | Yoon |
| 5,766,186 A | 6/1998 | Faraz et al. |
| 5,766,196 A | 6/1998 | Griffiths |
| 5,776,186 A | 7/1998 | Uflacker |
| 5,792,135 A | 8/1998 | Madhani et al. |
| 5,792,151 A | 8/1998 | Heck et al. |
| 5,797,927 A | 8/1998 | Yoon |
| 5,814,054 A | 9/1998 | Kortenbach et al. |
| 5,814,069 A | 9/1998 | Schulze et al. |
| 5,817,084 A | 10/1998 | Jensen |
| 5,846,254 A | 12/1998 | Schulze et al. |
| 5,860,992 A | 1/1999 | Daniel et al. |
| 5,865,836 A | 2/1999 | Miller |
| 5,871,488 A | 2/1999 | Tovey et al. |
| 5,878,193 A | 3/1999 | Wang et al. |
| 5,897,563 A | 4/1999 | Yoon et al. |
| 5,908,428 A | 6/1999 | Scirica et al. |
| 5,911,727 A | 6/1999 | Taylor |
| 5,938,668 A | 8/1999 | Scirica et al. |
| 5,941,430 A | 8/1999 | Kuwabara |
| 5,947,982 A | 9/1999 | Duran |
| 5,954,731 A | 9/1999 | Yoon |
| 5,954,733 A | 9/1999 | Yoon |
| 5,993,466 A | 11/1999 | Yoon |
| 6,016,905 A | 1/2000 | Gemma et al. |
| 6,056,771 A | 5/2000 | Proto |
| 6,071,289 A | 6/2000 | Stefanchik et al. |
| 6,086,601 A | 7/2000 | Yoon |
| 6,096,051 A | 8/2000 | Kortenbach et al. |
| 6,126,666 A | 10/2000 | Trapp et al. |
| 6,129,741 A | 10/2000 | Wurster et al. |
| 6,135,385 A | 10/2000 | Martinez de Lahidalga |
| 6,136,010 A | 10/2000 | Modesitt et al. |
| 6,138,440 A | 10/2000 | Gemma |
| 6,152,934 A | 11/2000 | Harper et al. |
| 6,214,030 B1 | 4/2001 | Matsutani et al. |
| 6,231,565 B1 | 5/2001 | Tovey et al. |
| 6,332,888 B1 | 12/2001 | Levy et al. |
| 6,332,889 B1 | 12/2001 | Sancoff et al. |
| 6,364,888 B1 | 4/2002 | Niemeyer et al. |
| 6,443,962 B1 | 9/2002 | Gaber |
| 6,454,778 B2 | 9/2002 | Kortenbach |
| 6,719,763 B2 | 4/2004 | Chung et al. |
| 6,719,764 B1 | 4/2004 | Gellman et al. |
| 6,743,239 B1 | 6/2004 | Kuehn et al. |
| 6,755,843 B2 | 6/2004 | Chung et al. |
| 6,783,524 B2 | 8/2004 | Anderson et al. |
| 6,783,537 B1 | 8/2004 | Kuhr et al. |
| 6,923,819 B2 | 8/2005 | Meade et al. |
| 6,936,054 B2 | 8/2005 | Chu |
| 6,939,358 B2 | 9/2005 | Palacios et al. |
| 6,955,643 B2 | 10/2005 | Gellman et al. |
| 7,004,951 B2 | 2/2006 | Gibbens, III |
| 7,041,111 B2 | 5/2006 | Chu |
| 7,131,979 B2 | 11/2006 | DiCarlo et al. |
| 7,144,401 B2 | 12/2006 | Yamamoto et al. |
| 7,232,447 B2 | 6/2007 | Gellman et al. |
| 7,235,087 B2 | 6/2007 | Modesitt et al. |
| 7,278,563 B1 | 10/2007 | Green |
| 7,338,504 B2 | 3/2008 | Gibbens, III et al. |
| 7,442,198 B2 | 10/2008 | Gellman et al. |
| 7,520,382 B2 | 4/2009 | Kennedy et al. |
| 7,524,320 B2 | 4/2009 | Tierney et al. |
| 7,582,096 B2 | 9/2009 | Gellman et al. |
| 7,588,583 B2 | 9/2009 | Hamilton et al. |
| 7,615,060 B2 | 11/2009 | Stokes et al. |
| 7,628,796 B2 | 12/2009 | Shelton, IV et al. |
| 7,637,369 B2 | 12/2009 | Kennedy et al. |
| 7,666,194 B2 | 2/2010 | Field et al. |
| 7,686,831 B2 | 3/2010 | Stokes et al. |
| 7,691,098 B2 | 4/2010 | Wallace et al. |
| 7,703,653 B2 | 4/2010 | Shah et al. |
| 7,763,036 B2 | 7/2010 | Stokes et al. |
| 7,766,925 B2 | 8/2010 | Stokes et al. |
| 7,770,365 B2 | 8/2010 | Enriquez, III et al. |
| 7,806,891 B2 | 10/2010 | Nowlin et al. |
| 7,815,654 B2 | 10/2010 | Chu |
| 7,824,401 B2 | 11/2010 | Manzo et al. |
| 7,828,812 B2 | 11/2010 | Stokes et al. |
| 7,833,235 B2 | 11/2010 | Chu |
| 7,833,236 B2 | 11/2010 | Stokes et al. |
| 7,842,048 B2 | 11/2010 | Ma |
| 7,846,169 B2 | 12/2010 | Shelton, IV et al. |
| 7,862,572 B2 | 1/2011 | Meade et al. |
| 7,862,575 B2 | 1/2011 | Tal |
| 7,862,582 B2 | 1/2011 | Ortiz et al. |
| 7,887,554 B2 | 2/2011 | Stokes et al. |
| 7,891,485 B2 | 2/2011 | Prescott |
| 7,896,890 B2 | 3/2011 | Ortiz et al. |
| 7,935,128 B2 | 5/2011 | Rioux et al. |
| 7,942,886 B2 | 5/2011 | Alvarado |
| 7,947,052 B2 | 5/2011 | Baxter, III et al. |
| 7,976,553 B2 | 7/2011 | Shelton, IV et al. |
| 7,976,555 B2 | 7/2011 | Meade et al. |

(56) References Cited

U.S. PATENT DOCUMENTS

| | | |
|---|---|---|
| 7,993,354 B1 | 8/2011 | Brecher et al. |
| 8,012,161 B2 | 9/2011 | Primavera et al. |
| 8,016,840 B2 | 9/2011 | Takemoto et al. |
| 8,048,092 B2 | 11/2011 | Modesitt et al. |
| 8,057,386 B2 | 11/2011 | Aznoian et al. |
| 8,066,737 B2 | 11/2011 | Meade et al. |
| 8,100,922 B2 | 1/2012 | Griffith |
| 8,118,820 B2 | 2/2012 | Stokes et al. |
| 8,123,762 B2 | 2/2012 | Chu et al. |
| 8,123,764 B2 | 2/2012 | Meade et al. |
| 8,136,656 B2 | 3/2012 | Kennedy et al. |
| 8,187,288 B2 | 5/2012 | Chu et al. |
| 8,196,739 B2 | 6/2012 | Kirsch |
| 8,206,284 B2 | 6/2012 | Aznoian et al. |
| 8,211,143 B2 | 7/2012 | Stefanchik et al. |
| 8,236,010 B2 | 8/2012 | Ortiz et al. |
| 8,236,013 B2 | 8/2012 | Chu |
| 8,246,637 B2 | 8/2012 | Viola et al. |
| 8,252,008 B2 | 8/2012 | Ma |
| 8,256,613 B2 | 9/2012 | Kirsch et al. |
| 8,257,369 B2 | 9/2012 | Gellman et al. |
| 8,257,371 B2 | 9/2012 | Hamilton et al. |
| 8,292,067 B2 | 10/2012 | Chowaniec et al. |
| 8,292,906 B2 | 10/2012 | Taylor et al. |
| 8,307,978 B2 | 11/2012 | Kirsch et al. |
| 8,361,089 B2 | 1/2013 | Chu |
| 8,366,725 B2 | 2/2013 | Chu |
| 8,372,090 B2 | 2/2013 | Wingardner et al. |
| 8,398,660 B2 | 3/2013 | Chu et al. |
| 8,460,320 B2 | 6/2013 | Hirzel |
| 8,469,973 B2 | 6/2013 | Meade et al. |
| 8,490,713 B2 | 7/2013 | Furnish et al. |
| 8,500,756 B2 | 8/2013 | Papa et al. |
| 8,512,243 B2 | 8/2013 | Stafford |
| 8,518,058 B2 | 8/2013 | Gellman et al. |
| 8,551,122 B2 | 10/2013 | Lau |
| 8,556,069 B2 | 10/2013 | Kirsch |
| 8,623,048 B2 | 1/2014 | Brecher et al. |
| 8,641,728 B2 | 2/2014 | Stokes et al. |
| 8,663,253 B2 | 3/2014 | Saliman |
| 8,696,687 B2 | 4/2014 | Gellman et al. |
| 8,702,729 B2 | 4/2014 | Chu |
| 8,709,021 B2 | 4/2014 | Chu et al. |
| 8,746,445 B2 | 6/2014 | Kennedy et al. |
| 8,747,304 B2 | 6/2014 | Zeiner et al. |
| 8,771,295 B2 | 7/2014 | Chu |
| 8,821,518 B2 | 9/2014 | Saliman et al. |
| 8,821,519 B2 | 9/2014 | Meade et al. |
| 8,920,440 B2 | 12/2014 | McClurg et al. |
| 8,920,441 B2 | 12/2014 | Saliman |
| 9,125,645 B1 | 9/2015 | Martin et al. |
| 2001/0027312 A1 | 10/2001 | Bacher et al. |
| 2002/0138084 A1* | 9/2002 | Weber .......... A61B 17/0469 606/139 |
| 2002/0193809 A1 | 12/2002 | Meade et al. |
| 2003/0083674 A1 | 5/2003 | Gibbens, III |
| 2003/0208100 A1 | 11/2003 | Levy |
| 2003/0233104 A1 | 12/2003 | Gellman et al. |
| 2004/0050721 A1 | 3/2004 | Roby et al. |
| 2004/0172047 A1 | 9/2004 | Gellman et al. |
| 2004/0260314 A1* | 12/2004 | Lizardi .......... A61B 17/0469 606/144 |
| 2005/0015101 A1 | 1/2005 | Gibbens, III et al. |
| 2005/0216038 A1 | 9/2005 | Meade et al. |
| 2006/0036232 A1 | 2/2006 | Primavera et al. |
| 2006/0047309 A1 | 3/2006 | Cichocki, Jr. |
| 2006/0069396 A1* | 3/2006 | Meade .......... A61B 17/0482 606/144 |
| 2006/0111732 A1 | 5/2006 | Gibbens et al. |
| 2006/0173491 A1 | 8/2006 | Meade et al. |
| 2006/0259073 A1 | 11/2006 | Miyamoto et al. |
| 2006/0281970 A1 | 12/2006 | Stokes et al. |
| 2006/0282096 A1 | 12/2006 | Papa et al. |
| 2006/0282097 A1 | 12/2006 | Ortiz et al. |
| 2006/0282098 A1 | 12/2006 | Shelton, IV et al. |
| 2006/0282099 A1 | 12/2006 | Stokes et al. |
| 2007/0088372 A1 | 4/2007 | Gellman et al. |
| 2007/0162052 A1 | 7/2007 | Hashimoto et al. |
| 2007/0173864 A1 | 7/2007 | Chu |
| 2007/0256945 A1 | 11/2007 | Kennedy et al. |
| 2008/0091220 A1 | 4/2008 | Chu |
| 2008/0103357 A1 | 5/2008 | Zeiner et al. |
| 2008/0109015 A1 | 5/2008 | Chu et al. |
| 2008/0132919 A1 | 6/2008 | Chui et al. |
| 2008/0177134 A1 | 7/2008 | Miyamoto et al. |
| 2008/0228204 A1 | 9/2008 | Hamilton et al. |
| 2008/0243146 A1 | 10/2008 | Sloan et al. |
| 2008/0255590 A1 | 10/2008 | Meade et al. |
| 2009/0024145 A1 | 1/2009 | Meade et al. |
| 2009/0205987 A1 | 8/2009 | Kennedy et al. |
| 2009/0209980 A1 | 8/2009 | Harris |
| 2009/0248041 A1 | 10/2009 | Williams et al. |
| 2009/0259092 A1 | 10/2009 | Ogdahl et al. |
| 2009/0287226 A1 | 11/2009 | Gellman et al. |
| 2009/0312772 A1 | 12/2009 | Chu |
| 2010/0010512 A1 | 1/2010 | Taylor et al. |
| 2010/0016866 A1 | 1/2010 | Meade et al. |
| 2010/0023024 A1 | 1/2010 | Zeiner et al. |
| 2010/0036415 A1 | 2/2010 | Cabezas |
| 2010/0042116 A1 | 2/2010 | Chui et al. |
| 2010/0063519 A1 | 3/2010 | Park et al. |
| 2010/0078336 A1 | 4/2010 | Reyhan et al. |
| 2010/0100125 A1 | 4/2010 | Mahadevan |
| 2010/0152751 A1 | 6/2010 | Meade et al. |
| 2010/0274265 A1 | 10/2010 | Wingardner et al. |
| 2011/0028999 A1 | 2/2011 | Chu |
| 2011/0040308 A1 | 2/2011 | Cabrera et al. |
| 2011/0042245 A1 | 2/2011 | McClurg et al. |
| 2011/0046642 A1 | 2/2011 | McClurg et al. |
| 2011/0046667 A1 | 2/2011 | Culligan et al. |
| 2011/0060352 A1 | 3/2011 | Chu |
| 2011/0082476 A1 | 4/2011 | Furnish et al. |
| 2011/0288582 A1 | 11/2011 | Meade et al. |
| 2011/0295278 A1 | 12/2011 | Meade et al. |
| 2011/0313433 A1 | 12/2011 | Woodard, Jr. et al. |
| 2012/0004672 A1 | 1/2012 | Giap et al. |
| 2012/0035626 A1 | 2/2012 | Chu |
| 2012/0041456 A1 | 2/2012 | Gellman et al. |
| 2012/0055828 A1 | 3/2012 | Kennedy et al. |
| 2012/0059396 A1 | 3/2012 | Harris et al. |
| 2012/0109163 A1 | 5/2012 | Chu et al. |
| 2012/0123471 A1 | 5/2012 | Woodard, Jr. et al. |
| 2012/0130404 A1 | 5/2012 | Meade et al. |
| 2012/0143248 A1 | 6/2012 | Brecher et al. |
| 2012/0150199 A1 | 6/2012 | Woodard, Jr. et al. |
| 2012/0165837 A1 | 6/2012 | Belman et al. |
| 2012/0165838 A1 | 6/2012 | Kobylewski et al. |
| 2012/0215234 A1 | 8/2012 | Chowaniec et al. |
| 2012/0226292 A1 | 9/2012 | Hirzel |
| 2012/0228163 A1 | 9/2012 | Kirsch |
| 2012/0232567 A1 | 9/2012 | Fairneny |
| 2012/0283748 A1 | 11/2012 | Ortiz et al. |
| 2012/0283750 A1 | 11/2012 | Saliman et al. |
| 2012/0283755 A1 | 11/2012 | Gellman et al. |
| 2013/0041388 A1 | 2/2013 | Lane et al. |
| 2013/0282027 A1 | 10/2013 | Woodard, Jr. et al. |
| 2013/0282031 A1 | 10/2013 | Woodard, Jr. et al. |
| 2013/0331866 A1 | 12/2013 | Gellman et al. |
| 2014/0088621 A1 | 3/2014 | Krieger et al. |
| 2014/0166514 A1 | 6/2014 | Martin et al. |
| 2014/0171970 A1 | 6/2014 | Martin et al. |
| 2014/0171971 A1 | 6/2014 | Martin et al. |
| 2014/0171972 A1 | 6/2014 | Martin |
| 2014/0171975 A1 | 6/2014 | Martin et al. |
| 2014/0171976 A1 | 6/2014 | Martin et al. |
| 2014/0171977 A1 | 6/2014 | Martin et al. |
| 2014/0171978 A1 | 6/2014 | Martin |
| 2014/0171979 A1 | 6/2014 | Martin et al. |
| 2014/0172015 A1 | 6/2014 | Martin et al. |
| 2015/0127024 A1 | 5/2015 | Berry |
| 2015/0351745 A1 | 12/2015 | Mumaw et al. |
| 2015/0351746 A1 | 12/2015 | Martin et al. |
| 2015/0351747 A1 | 12/2015 | Martin et al. |

(56) References Cited

U.S. PATENT DOCUMENTS

| | | | |
|---|---|---|---|
| 2015/0351748 A1 | 12/2015 | White et al. |
| 2015/0351749 A1 | 12/2015 | Martin et al. |
| 2015/0351756 A1 | 12/2015 | Martin et al. |

FOREIGN PATENT DOCUMENTS

| | | |
|---|---|---|
| EP | 0739184 B1 | 9/1998 |
| EP | 1791476 A2 | 6/2007 |
| EP | 2292157 A2 | 3/2011 |
| EP | 2308391 A1 | 4/2011 |
| FR | 2540377 A1 | 8/1984 |
| GB | 18602 A | 0/1909 |
| GB | 2389313 A | 12/2003 |
| JP | S55-151956 A | 11/1980 |
| WO | WO 95/19149 A1 | 7/1995 |
| WO | WO 97/29694 A1 | 8/1997 |
| WO | WO 99/12482 A1 | 3/1999 |
| WO | WO 99/40850 A1 | 8/1999 |
| WO | WO 99/47050 A1 | 9/1999 |
| WO | WO 01/12084 A1 | 2/2001 |
| WO | WO 02/102226 A2 | 12/2002 |
| WO | WO 03/028541 A2 | 4/2003 |
| WO | WO 2004/012606 A1 | 2/2004 |
| WO | WO 2004/021894 A1 | 3/2004 |
| WO | WO 2006/034209 A2 | 3/2006 |
| WO | WO 2007/089603 A2 | 8/2007 |
| WO | WO 2008/045333 A2 | 4/2008 |
| WO | WO 2008/045376 A2 | 4/2008 |
| WO | WO 2008/081474 A1 | 7/2008 |
| WO | WO 2008/147555 A2 | 12/2008 |
| WO | WO 2010/062380 A2 | 6/2010 |
| WO | WO 2012/044998 A2 | 4/2012 |
| WO | WO 2012/068002 A1 | 5/2012 |
| WO | WO 2012/088232 A3 | 6/2012 |
| WO | WO 2013/142487 A1 | 9/2013 |
| WO | WO 2014/162434 A1 | 10/2014 |

OTHER PUBLICATIONS

U.S. Appl. No. 13/832,660, filed Mar. 15, 2013 by Ethicon Endo-Surgery, Inc.
U.S. Appl. No. 13/832,709, filed Mar. 15, 2013 by Ethicon Endo-Surgery, Inc.
U.S. Appl. No. 13/832,786, filed Mar. 15, 2013 by Ethicon Endo-Surgery, Inc.
U.S. Appl. No. 13/832,816, filed Mar. 15, 2013 by Ethicon Endo-Surgery, Inc.
U.S. Appl. No. 13/832,867, filed Mar. 15, 2013 by Ethicon Endo-Surgery, Inc.
U.S. Appl. No. 13/832,897, filed Mar. 15, 2013 by Ethicon Endo-Surgery, Inc.
U.S. Appl. No. 13/832,986, filed Mar. 15, 2013 by Ethicon Endo-Surgery, Inc.
U.S. Appl. No. 13/833,042, filed Mar. 15, 2013 by Ethicon Endo-Surgery, Inc.
U.S. Appl. No. 13/833,121, filed Mar. 15, 2013 by Ethicon Endo-Surgery, Inc.
Endo 360 "Laparoscopic & Minimally Invasive Suturing Devices" Catalog—2 Pages—EndoEvolution, LLC—2011.
Covidien Endo Stitch (Features and Benefits) "Suturing Made Easy" Brochure—4 Pages—2008.
Pages from www.endoevolution.com. Printed on Jun. 3, 2014, but publication date unknown. Please treat as prior art until applicant establishes otherwise.
U.S. Appl. No. 13/792,976, filed Mar. 11, 2013 by Ethicon Endo-Surgery, Inc.
U.S. Appl. No. 13/793,048, filed Mar. 11, 2013 by Ethicon Endo-Surgery, Inc.
U.S. Appl. No. 29/493,229, filed Jun. 6, 2014 by Ethicon Endo-Surgery, Inc.
U.S. Appl. No. 29/493,231, filed Jun. 6, 2014 by Ethicon Endo-Surgery, Inc.
U.S. Appl. No. 14/298,083, filed Jun. 6, 2014 by Ethicon Endo-Surgery, Inc.
U.S. Appl. No. 14/600,486, filed Jan. 20, 2015 by Ethicon Endo-Surgery, Inc.
U.S. Appl. No. 29/493,233, filed Jun. 6, 2014 by Ethicon Endo-Surgery, Inc.
U.S. Appl. No. 14/688,497, filed Apr. 16, 2015 by Ethicon Endo-Surgery, Inc.
U.S. Appl. No. 14/721,244, filed May 26, 2015 by Ethicon Endo-Surgery, Inc.
U.S. Appl. No. 14/721,251, filed May 26, 2015 by Ethicon Endo-Surgery, Inc.
U.S. Appl. No. 14/741,849, filed Jun. 17, 2015 by Ethicon Endo-Surgery, Inc.
U.S. Appl. No. 29/530,605, filed Jun. 18, 2015 by Ethicon Endo-Surgery, Inc.
International Preliminary Report Dated Jun. 16, 2015, International Application No. PCT/US2013/074866.
International Search Report Dated May 6, 2014, International Application No. PCT/US2013/074866.
International Search Report Dated Sep. 15, 2015, International Application No. PCT/US2015/031883.
International Search Report Dated Sep. 28, 2015, International Application No. PCT/US2015/031911.
European Search Report Dated Feb. 3, 2016; Application No. 15176794.4.
European Search Report Dated Dec. 7, 2015; Application No. 15176796.9.
European Search Report Dated Dec. 4, 2015; Application No. 15176924.7.
European Search Report Dated Nov. 30, 2015; Application No. 15176774.6.

* cited by examiner

JAWED RECEIVER FOR NEEDLE CARTRIDGE

BACKGROUND

The present invention relates in general to surgical devices and procedures, and more particularly to surgical suturing.

Sutures are often used in a wide variety of surgical procedures. Manual suturing is typically accomplished by the surgeon using a fine pair of graspers to grab and hold a suture needle, pierce the tissue with the needle, let go of the needle, and regrasp the needle to pull the needle and accompanying suture thread through the tissues to be sutured. Such needles are typically curved with the suture attached to the trailing end of the needle. A variety of automated suturing devices have been attempted to speed the process of suturing and to facilitate fine suturing or suturing during endoscopic, laparoscopic, or arthroscopic surgeries. While automated suturing devices are generally known, no one has previously made or used a surgical suturing device in accordance with the present invention.

BRIEF DESCRIPTION OF DRAWINGS

While the specification concludes with claims which particularly point out and distinctly claim the invention, it is believed the invention will be better understood from the following description taken in conjunction with the accompanying drawings illustrating some non-limiting examples of the invention. Unless otherwise indicated, the figures are not necessarily drawn to scale, but rather to illustrate the principles of the invention.

SUMMARY

Figure 1:
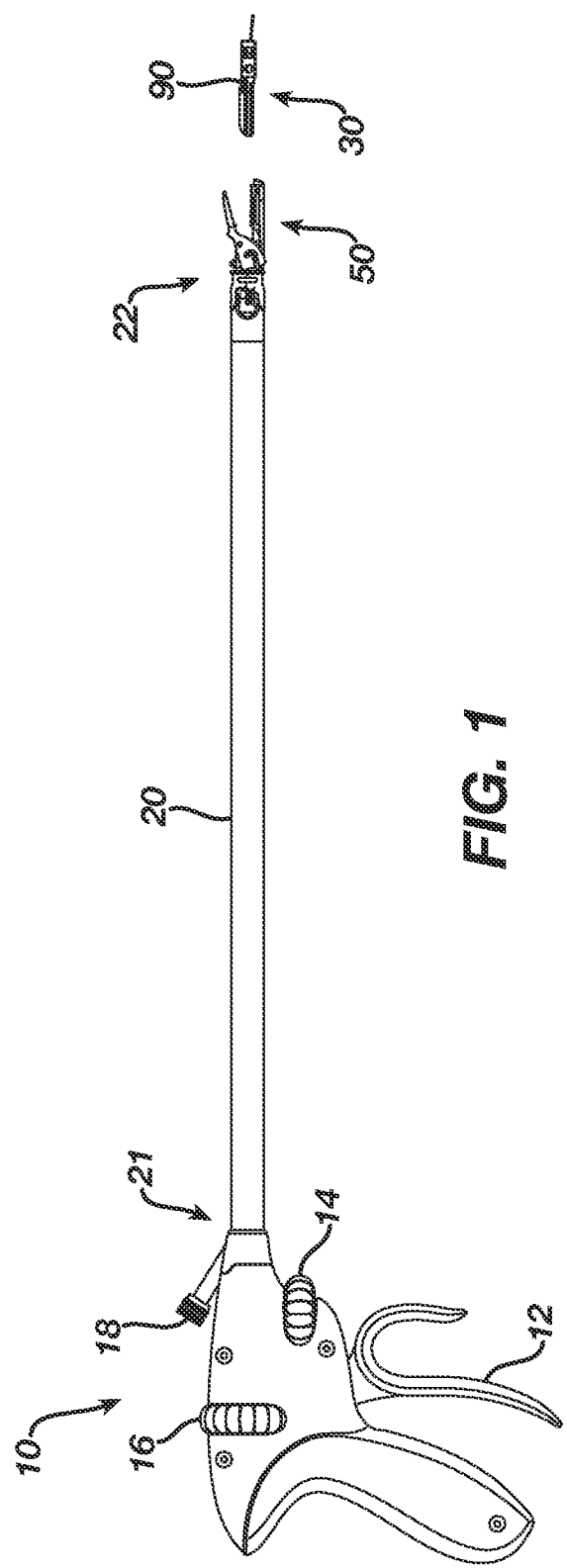
FIG. 1 depicts a side view of a surgical suturing device.

In one embodiment, a surgical suturing device comprises a cartridge having a needle and suture, an elongate shaft having a proximal end and a distal end, an actuator connected to the proximal end of the elongate shaft, and a receiver connected to the distal end of the elongate shaft. The receiver comprises a pair of jaws having a closed position adapted to receive and retain the cartridge and an opened position adapted to release the cartridge.

The actuator may comprise a handle. The jaws may comprise a stationary jaw and a pivoting jaw. The stationary jaw may comprise a rotary drive and the cartridge comprises a rotary input adapted to engage the rotary drive. The stationary jaw may comprise two longitudinal rails dimensioned and adapted to receive the cartridge and laterally retain the cartridge. The pivoting jaw may comprise a resiliently biased tooth oriented toward the stationary jaw, the tooth being dimensioned and adapted to engage and distally retain the cartridge. The surgical suturing device may further comprise a spring biasing the pivoting jaw towards the closed position. The pivoting jaw may comprise a second opened position spaced further from the stationary jaw than in the opened position, wherein in the second opened position the spring does not bias the pivoting jaw towards the closed position.

The surgical suturing device may further comprise a button operative to move the jaws from the closed position to the opened position. The button may be positioned adjacent the jaws. The surgical suturing device may comprise a follower connected to the button, the follower moves in a cam slot, and wherein actuation of the button drives the follower along the cam slot to open and close the jaws. A spring may act on the button and bias the jaws closed.

In another embodiment, a surgical suturing device comprises a cartridge comprising a needle and suture. An elongate shaft has a proximal end and a distal end. An actuator is connected to the proximal end of the elongate shaft. A pair of jaws is connected to the distal end of the elongate shaft. The jaws have a closed position adapted to receive and retain the cartridge, and wherein the jaws are latched in the closed position, a partially opened position adapted to release the cartridge wherein the jaws are biased by a spring from the first opened position towards the closed position, and a fully opened position spaced apart further than the partially opened position, wherein spring does not bias the jaws towards the closed position.

The surgical suturing device may further comprise a button adjacent the jaws operable to unlatch the jaws from the closed position. The jaws may comprise a stationary jaw and a pivoting jaw that pivots about an axis. The surgical suturing device may further comprise a cam slot on the pivoting jaw and a follower on the button, wherein the follower moves in the cam slot between a first position, a second position, and a third position, the cam slot having a first cam profile between the first and second positions and second cam profile between the second and third positions. In the first position the follower engages the cam slot so as to prevent the jaws from opening thereby latching the jaws in the closed position. Actuation of the button moves the follower along the first cam profile to unlatch the jaws and to move the jaws to the first opened position. The second cam profile is substantially equidistant from the axis.

In another embodiment, a surgical suturing device comprises a cartridge having a needle and suture. An elongate shaft has a proximal end and a distal end. An actuator is connected to the proximal end of the elongate shaft. A receiver is connected to the distal end of the elongate shaft. The receiver comprises a means for retaining and releasing the cartridge.

In yet another embodiment, a surgical suturing device comprises an arced needle comprises a length of suture. A needle driver is operable to engage and rotate the needle in a circular path. The needle driver reciprocates between a drive stoke wherein the needle is rotated and a return stroke. A trigger is operably connected to the needle driver, wherein moving the trigger in a first direction actuates the needle driver through its drive stroke, and moving the trigger in a second direction actuates the needle driver through its return stroke. A ratchet mechanism preventing the trigger from moving in the second direction until the needle driver has been actuated through the drive stroke.

The drive stroke may rotate the needle through an angular arc. The angular arc may be about 180 degrees. The needle may be restrained from rotating during the return stroke. The ratchet mechanism may comprise a pawl and a rack, the rack comprising a first end, a second end, and the length extending between the first and second ends. The rack may comprise a plurality of teeth along the length. The pawl may pivots between a first trailing oblique angle relative the rack in the first direction and a second trailing oblique angle relative the rack in the second direction. The pawl may pivot between the first and second trailing oblique angles upon reaching the first and second ends, respectively. The pawl may reset upon reaching the first and second ends of the rack. The ratchet mechanism may be bi-directional preventing the trigger from moving in the first direction until the needle driver has been actuated through the return stroke.

In another embodiment, a surgical suturing device comprises an arced needle comprises a length of suture. A needle driver is operable to engage and rotate the needle in a circular path. The needle driver reciprocates between a drive stoke wherein the needle is rotated about 180 degrees and return stroke where the needle is constrained from rotating. A trigger is operably connected to the needle driver, wherein moving the trigger in a first direction actuates the needle driver through its drive stroke, and moving the trigger in a second direction actuates the needle driver through its return stroke. A bi-directional ratchet mechanism is connected to the trigger. The bi-directional ratchet mechanism prevents the trigger from moving in the second direction until the needle driver has been actuated through the drive stroke, and prevents the trigger from moving in the first direction until the needle driver has been actuated through the return stroke.

The bi-directional ratchet mechanism may comprise a pawl and a rack, the rack having a first end, a second end, and the length extending between the first and second ends. The pawl may reset upon reaching the first and second ends of the rack. The rack may comprise a plurality of teeth along the length.

In yet another embodiment, a surgical suturing device comprises an arced needle comprises a length of suture. An elongate shaft comprises a proximal end and a distal end. A needle driver is on the distal end of the elongate shaft operable to engage and rotate the needle in a circular path. The needle driver reciprocates between a drive stroke wherein the needle is rotated and a return stroke. A trigger is on the proximal end of the elongate shaft. A drive rod in the elongate shaft operably connects the trigger and the needle driver. Moving the trigger in a first direction actuates the needle driver through its drive stroke, and moving the trigger in a second direction actuates the needle driver through its return stroke. A spring is operably connected to the drive rod limiting a load transmitted through the drive rod. The spring may limit the load transmitted through the drive rod when the trigger is moved in a first direction.

In another embodiment, a surgical suturing device comprises an arced needle comprises a length of suture. An elongate shaft comprises a proximal end and a distal end. A needle driver is on the distal end of the elongate shaft operable to engage and rotate the needle in a circular path. The needle driver reciprocates between a drive stroke wherein the needle is rotated and a return stroke. An actuator is on the proximal end of the elongate shaft. A drive rod is in the elongate shaft operably connected to the needle driver. A mechanical linkage comprises a force limiting spring connects the actuator to the drive rod.

The surgical suturing device may further comprise a rack and pinion drive interposed between the drive rod and the needle driver. The mechanical linkage may comprise a sled axially traversable relative to the drive rod, and the spring is positioned around drive rod and within the sled. The actuator may be a trigger, and the device may further comprise a link connecting the trigger to the sled. The sled may have a distal end and a proximal end, and the drive rod may have a flange, and the spring may be interposed between the flange and the distal end of the sled, and the flange may directly engage the proximal end of the sled. A link may connect the sled to the actuator.

In yet another embodiment, a surgical instrument comprises an elongate shaft having a proximal end, a distal end, and an articulating portion. An end effector is on the distal end and an actuator is on the proximal end. A rod is in the shaft having a proximal end with a cam follower, a distal end operably connected to the articulation portion, and a longitudinal axis extending between the proximal and distal ends. A disk is in the actuator rotatable in response to user input in a plane substantially parallel to the longitudinal axis of the rod. The disk has a cam slot receiving the cam follower such that rotation of the disk moves the rod longitudinally to articulate the elongate shaft at the articulation portion.

The end effector may comprise a circular needle applier. The cam follower may be oriented substantially normal to the rod and normal to the disk. The cam slot may comprise a length having angular and radial components relative to the disk. The cam slot may comprise a tangent axis where the cam slot is engaged by the cam follower, the tangent axis being substantially normal to the longitudinal axis of the rod. The tangent axis may be substantially normal to the longitudinal axis of the rod throughout the length of the cam slot. The cam follower may be offset from the longitudinal axis of the rod. The cam follower may be medial to the longitudinal axis of the rod. The articulating portion may comprise an articulation joint. A rotary input knob may be connected to the disk.

The surgical instrument may further comprise a second rod in the shaft having a proximal end with a cam follower, a distal end operably connected to the articulation portion, and a longitudinal axis extending between the proximal and distal ends. A second cam slot on the disk receives the second cam follower such that rotation of the disk moves the second rod longitudinally to articulate the elongate shaft at the articulation portion.

The surgical instrument may further comprise at least one detent on the cam slot. The cam follower may include a straight portion that closely fits in the cam slot and a radius portion dimensioned to be received by the at least one detent. As the disk rotates the radius portion raises and lowers into the at least one detent and the straight portion follows and remains engaged in the cam slot.

In another embodiment, a suturing device comprises an elongate shaft having a proximal end, a distal end, and an articulation joint. A circular needle applier is on the distal end of the elongate shaft. An actuator is on the proximal end of the elongate shaft. First and second rods are in the elongate shaft each having a proximal end with a cam follower, a distal end operably connected to the articulation joint, and a longitudinal axis extending between the proximal and distal ends. A disk is in the actuator rotatable in response to user input in a plane substantially parallel to the longitudinal axes of the elongate shafts. The disk has first and second helical cam slots receiving the first and cam followers, respectively. Clockwise rotation of the disk moves the first rod distally and the second rod proximally to articulate the joint in a first direction, and counterclockwise rotation of the disk moves the first rod proximally and the second rod distally to articulate the joint in a second direction.

The first and second cam slots each may comprise a tangent axis where the cam slot is engaged by the respective first and second cam followers, the tangent axes each being substantially normal to the longitudinal axis of the first and second rods. The cam followers may be medial to the longitudinal axis of the respective rod. The actuator may comprise a handle.

DETAILED DESCRIPTION

FIG. 1 illustrates an embodiment of a surgical suturing device. An elongate shaft (20) has a proximal end (21), a distal end (22), and a longitudinal axis extending therebetween. An actuator (10) is connected to the proximal end (21) of the shaft (20). In this embodiment the actuator (10) is a manual pistol grip handle; however, a variety of other manual actuators could also be used, including a scissor grip handle, a syringe grip handle, endoscopic rotary knobs, and the like. The actuator (10) could also take the form of a robotic interface, such as a DAVINCI puck, or a housing comprising gears or pulleys, servomechanisms, and the like.

A circular needle applier (30) is connected to the distal end (22) of the shaft (20). The circular needle applier (30) rotates an arced needle in a circular path enabling a surgeon to selectively apply sutures. The circular needle applier (30) may be integral with the shaft (20) and actuator (10) as a unitary disposable instrument intended for a single surgical procedure. The circular needle applier (30) may also be integral with the shaft (20) and actuator (10) as a reusable instrument. Optionally, as illustrated here, the circular needle applier (30) may be embodied in a disposable cartridge (90) and the shaft (20) may include a receiver (50) to hold the cartridge (90). In such an embodiment, the shaft (20) and actuator (10) may also be disposable or reusable. Embodiments with reusable components are intended to be cleaned, sterilized, and reused for a multiple surgical procedures, and may include a flush port (18) to facilitate cleaning. The preferable life cycle of a reusable instrument is at least 50 operations, more preferably at least 150 operations, and most preferably at least 200 operations. Reusable components may be built using materials that can withstand autoclave sterilization temperatures of at least 135 degrees Celsius, although low temperature materials can also used with low temperature sterilization techniques known in the art.

A first input (12), shown here as a trigger that pivots between opened and closed positions, may be used to selectively actuate the circular needle applier (30). The trigger may be spring biased to return the trigger to its open position. A second input (14), shown here as a rotary knob, may be used to selectively articulate the shaft (20). A third input (16), shown here as a rotary knob, may be used to selectively rotate the circular needle applier (30) about the shaft (20). Naturally, the number, type, configuration, and operation of the inputs (12, 14, and 16) may vary.

Examples of surgical suturing devices and subcomponents are disclosed in co-owned U.S. application Ser. No. 13/832,595 filed 15 Mar. 2013, the disclosure of which is incorporated herein by reference. Many of the teachings disclosed in that application are applicable to the present disclosure.

Figure 2A:
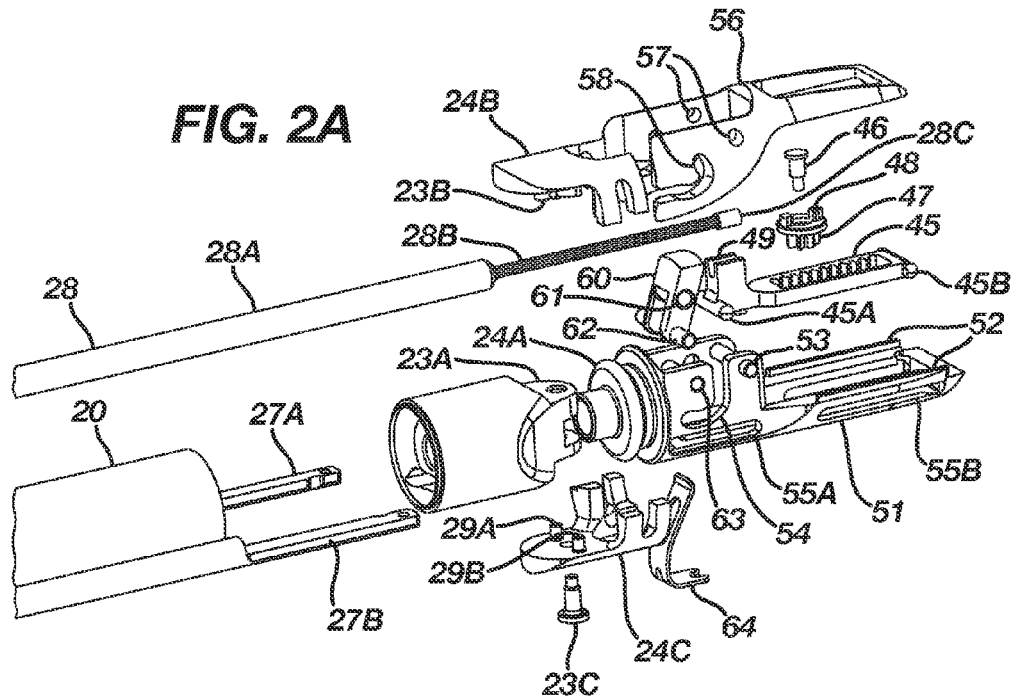
FIG. 2A depicts top perspective exploded view of a receiver.
Figure 2B:
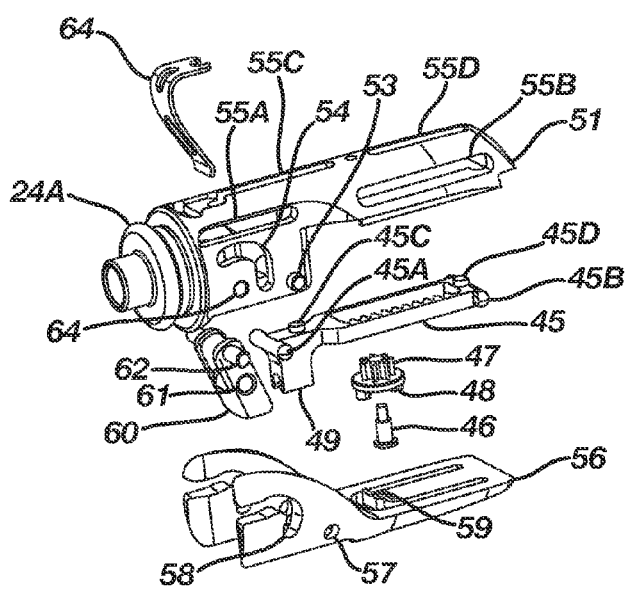
FIG. 2B depicts bottom perspective exploded view of a receiver.

FIGS. 2A-B illustrate exploded views of an embodiment of a receiver (50). The shaft distal end (22) comprises an articulation joint (23) and a rotational bearing (24). The joint (23) includes a knuckle (23A) that receives pins (23B, C) connected to the bearing supports (24B, C). Thus, the pins (23B, C) define the pivoting axis for the joint (23) enabling the receiver (50) to articulate left and right relative the shaft (20). Rods (27A, B) are operably connected to the joint (23). In this embodiment the rods (27A, B) extend through the shaft (20), through the knuckle (23A), and connect to pins (29A, B) on the bearing support (24C). The rods (27A, B) are operatively connected to the second input (14) to alternately push and pull the rods (27A, B). Because the pins (29A, B) are laterally spaced from the pivoting axis, the push and pull action will in turn articulate the receive (50) about the joint (23) relative the shaft (20).

The rotational bearing (24) is positioned distal to the articulation joint (23). The bearing (24) includes a circumferential flange (24A) captured between the bearing supports (24B, 24C) such that the flange (24A) can rotate relative the bearing supports (24B, 24C) and enabling unbounded rotation of the receiver (50) relative the shaft (20). A drive rod (28) extends through the shaft (20). In this embodiment the drive rod (28) comprises a proximal rigid portion (28A) and a distal bendable portion (28B) fixedly connected to one another. The bendable portion (28B) extends through the joint (23) and through the bearing (24), and the distal end (28C) is fixedly connected to the mount (49) on the rack (45).

The rack (45) reciprocates longitudinally in the lower jaw (51) with the followers (45A, B, C and D) constrained in tracks (55A, B, C, and D), respectively. The tracks (55A, B, C, and D) open through the lower jaw (51) providing fluid passages to the internal components within the lower jaw (51), thus facilitating easier cleaning. A pinion (47) is mounted to the lower jaw (51) by the pin (46) in the rack (45) such that longitudinal reciprocation of the rack (45) is translated to rotational reciprocation of the pinion (47). The key (48) translates the reciprocating rotation to the transmission in the cartridge (90), which in turn actuates the circular needle applier (30).

The drive rod (28) is operatively connected to the first input (12) and to the third input (16). Actuation of the first input (12) will impart axial push and pull loads on the drive rod (28) to longitudinally reciprocate the rack (45) and actuate the circular needle applier (30). Actuation of the third input (16) will impart a rotational load on the drive rod (28) thus rotating the receiver (50) about the bearing (24) relative to the shaft (20). Accordingly, a single drive rod (28) operates to both actuate the circular needle applier (30) as well as control distal rotation. By consolidating dual functions with a single drive rod (28), the number of components is reduced, and more space is provided in the shaft (20), making the device less expensive to manufacture and easier to clean.

The receiver (50) is dimensioned and adapted to receive and hold a disposable cartridge (90). The receiver has upper and lower jaws (56, 51) having a closed position adapted to receive and retain the cartridge (90) and an opened position adapted to release the cartridge. In this embodiment, the lower jaw (51) is stationary and the upper jaw (56) pivots; however, the arrangement could be reversed, or in an alternative embodiment both jaws (56, 51) could pivot. The lower jaw (51) has two laterally offset longitudinal rails (52) dimensioned and adapted to receive the cartridge (90). The rails (52) help longitudinally align the cartridge (90) in the receiver (50) and laterally retain the cartridge (90) in the jaws (51, 56). The upper jaw (56) pivots relative the lower jaw (51) about the pin (53) that is received in the holes (57). A tooth (59) is resiliently oriented downward from the upper jaw (56) toward the lower jaw (51) with a ramped distal face and a stepped proximal face. The tooth (59) is dimensioned and adapted to latch with the cartridge (90) and longitudinally retain the cartridge in the jaws (51, 56). The tooth (59) deflects by virtue of a resilient cantilevered arm extending proximally from the distal end of the upper jaw (56). In this embodiment the tooth (59) and cantilevered arm are monolithic with the upper jaw (56), thus reducing the number of components and moving pieces, making the device less expensive to manufacture and easier to clean.

The button (60) is used to open and close the jaws (51, 56). While the button (60) could be place on or near the actuator (10), in this embodiment the button (60) is positioned adjacent the receiver (50), which eliminates a linkage in the shaft (20) thus creating space in the shaft (20) and making the device less expensive and easier to clean. The action of the button (60) may vary, but in this embodiment the button (60) pivots relative the lower jaw (51) about the pin (63) that is received hole (61). The follower (62) is received by the cam slots (54, 58). Pivoting the button (60) proximally will open the jaws (51, 56), while pivoting the jaws distally will close the jaws (51, 56). The spring (64) engages and biases the button (60) distally. By pulling the button (60) proximally, the follower (62) will drive the cam slot (58) to open the upper jaw (56). When the button (60) is released, the spring (64) will bias the button (60) distally to close the upper jaw (56).

Figure 3A:
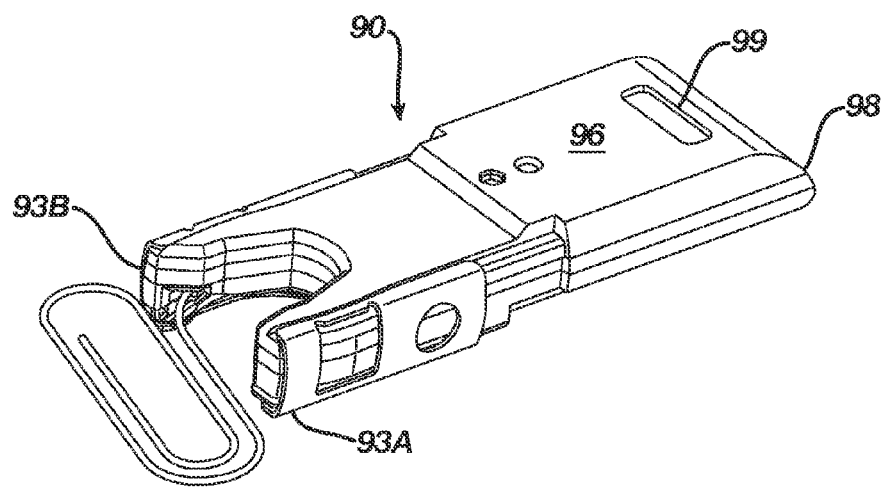
FIG. 3A depicts a top perspective view of a cartridge.
Figure 3B:
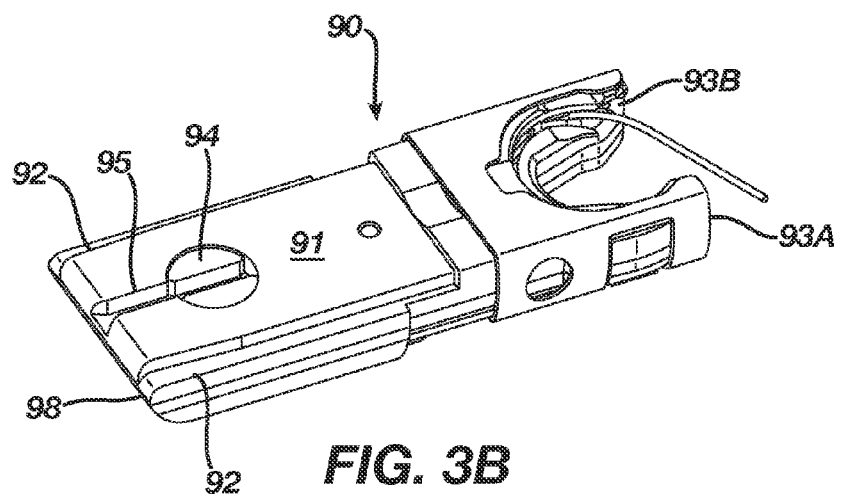
FIG. 3B depicts a bottom perspective view of a cartridge.

FIGS. 3A-B illustrate one embodiment of a disposable needle driver cartridge (90) adapted to be attached to the receiver (50). The lower face (91) is adapted to engage the lower jaw (51) and the upper face (96) to engage the upper jaw (56). Features on the cartridge (90) prevent improper insertion of the cartridge (90) into the receiver (50), but also contribute to the aesthetic appearance of the cartridge (90). For instance, the lower face (91) has a pair of longitudinal notched shoulders (92) dimensioned to interface and mate with the rails (52). In this embodiment, the notched shoulders (92) are shaped as a stepped rabbet, but a variety of other aesthetic shapes could also be employed such as chamfers and radii. In contrast, the upper face (96) is asymmetrical relative the lower face (91) and lacks shoulder notches, so the upper face (96) would interfere with the rails (52) if the cartridge was inserted upside-down. In another instance, the geometry of the proximal face (98) is vertically asymmetrical thus prevents the cartridge (90) from being inserted upside-down between the jaws (51, 56). In this embodiment, the proximal face (98) comprises a curved surface that gently transition to the upper face (96), which matches similar geometry in the receiver (50), while the transition to the lower face (91) has a tighter radius. Naturally, a variety of other asymmetrical aesthetic geometries could also be employed that could contribute to the visual appearance of the cartridge (90).

The arms (93A, B) define a generally U-shaped distal end on the cartridge (90). The slot (95) and rotary input (94) are aligned and dimensioned to receive the key (48) while the cartridge (90) is being slid into the receiver (50). When the cartridge (90) is fully seated into the receiver (50), the step (99) aligns with and receives the tooth (59) to latch the cartridge (90) in the receiver (50). The key (48) also aligns with rotary input (94) thereby providing a torsional interface that rotationally couples the pinion (47) and rotary input (94). In use, the needle (70) exits arm (93A) and enters arm (93B).

Figure 4:
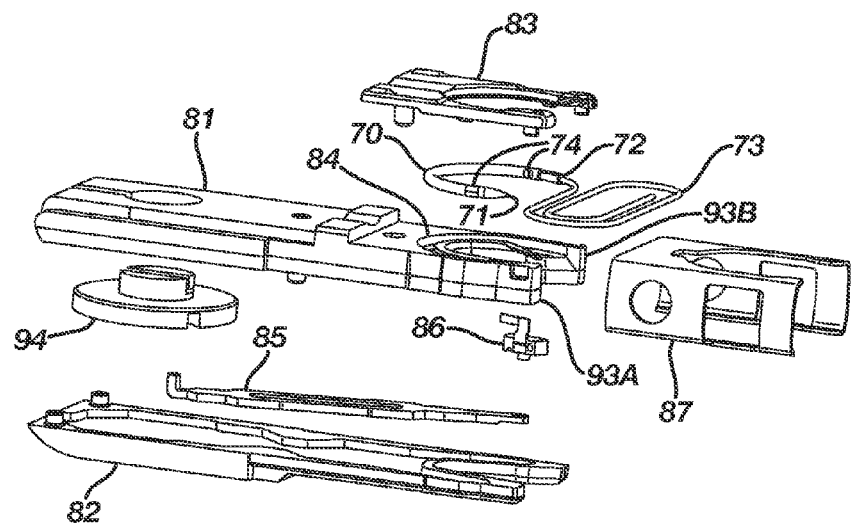
FIG. 4 depicts an exploded view of a cartridge.

FIG. 4 illustrates an example of a cartridge (90) comprising a lower body (81), an upper body (82), and a needle cover (83). The needle driver (86), rotary input (94), and link (85) are captured between the lower body (81) and an upper body (82). The lower and upper bodies (81, 82) are attached to one another using a variety of known techniques, including welds, pins, adhesives, and the like to form the cartridge body. The needle (70) has a leading end (71) and a length of suture (73) extending from the trailing end (72). The needle (70) rotates in a circular path defined by the needle track (84) and between the arms (93A, B). Features (74) may be provided to facilitate the needle driver (86) to engage and drive the needle (70). The needle (70) is captured in the needle track (84) by the needle cover (83). The cage (87) slides over the cartridge body to attach the needle cover (83) against the lower body (81).

Figure 5A:
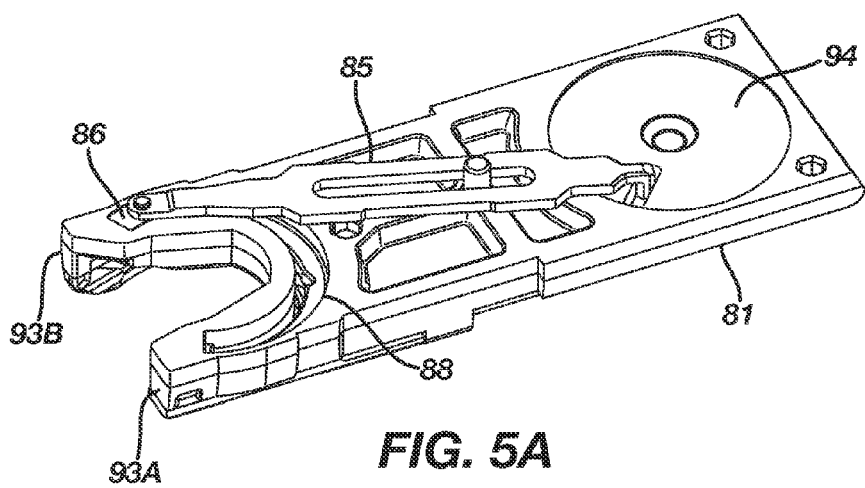
FIG. 5A depicts a perspective view of a transmission for driving a needle at one end of its stroke.
Figure 5B:
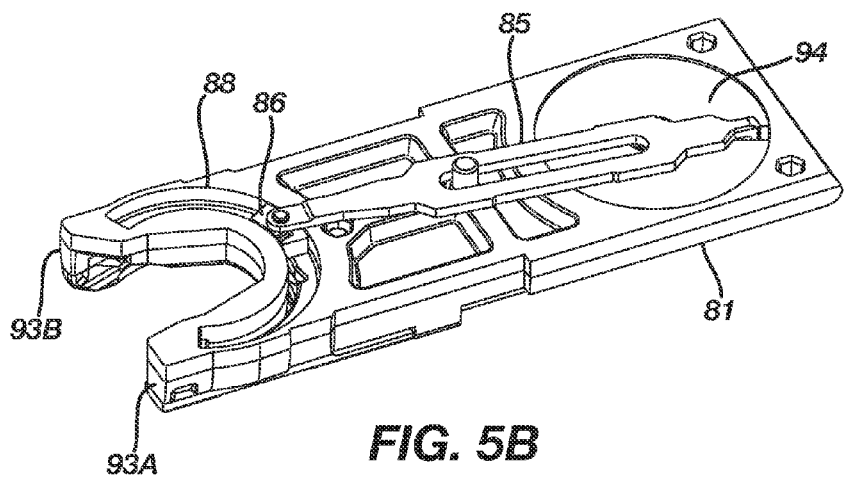
FIG. 5B depicts a perspective view of a transmission for driving a needle at mid-stroke.
Figure 5C:
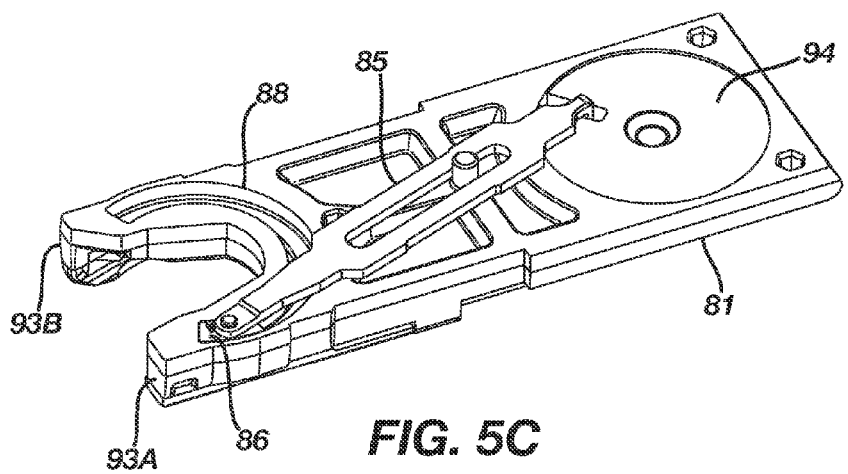
FIG. 5C depicts a perspective view of a transmission for driving a needle at the other end of its stroke.

FIGS. 5A-C illustrate an embodiment of a drive stroke of the transmission in the cartridge (90) for driving a needle (70) in a circular path. The needle driver (86) rides in the carrier track (88) and extends into the needle track (84) to engage and drive the needle (70). A link (85) connects the rotary input (94) to the needle driver (86). FIG. 5A illustrates the needle driver (86) positioned at one end of its stroke in the carrier track (88). As shown in FIG. 5B, counterclockwise rotation of the rotary input (94) will translate the needle driver (86) clockwise along the carrier track (88) driving the needle (70) clockwise. As shown in FIG. 5C, continued counterclockwise rotation of the rotary input (94) will continue to translate the needle driver (86) and drive the needle (70) clockwise until it reaches the other end of its stroke in the carrier track (88). In this embodiment, the drive stroke rotates the needle (70) in its circular path about 180 degrees. For the return stroke, the sequence can be reversed by rotating the rotary input (94) clockwise, which will translate the needle driver (86) counterclockwise in the carrier track (88). Thus, a sequence of drive and return strokes will rotate the needle (70) in a circular path.

FIGS. 6A-D illustrate an example of the operation of a receiver (50). The button (60) drives the follower (62) along the cam slot (58) in the upper jaw (56). The cam slot (58) includes three profiles (58A-C). The first profile (58A) is used to assemble the receiver (50). The first profile (58A) transitions to the second profile (58B) that is used to move the upper jaw (56) between its closed and partially opened positions. The second profile (58B) transitions to the third profile (58C) that is used to move the upper jaw (56) between its partially opened and fully opened positions.

Figure 6A:
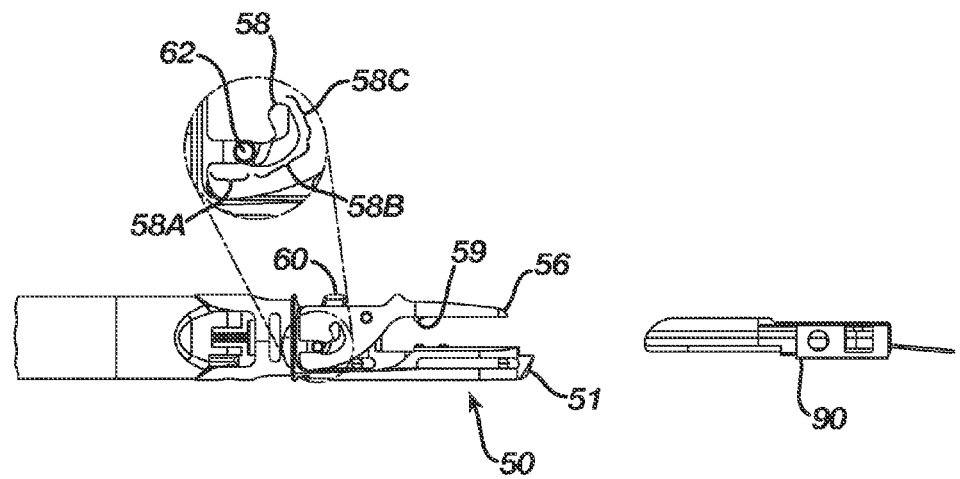
FIG. 6A depicts a side view of a receiver and a detached cartridge.
Figure 6B:
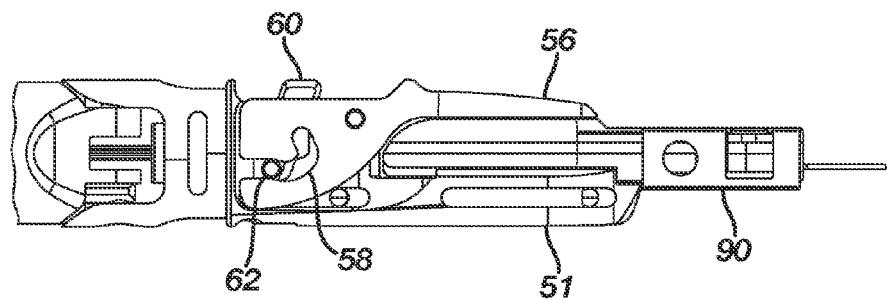
FIG. 6B depicts a side view of a receiver and an attached cartridge.

The cartridge (90) is loaded into the receiver (50) with the jaws (51, 56) in their closed position. As shown in FIGS. 6A-B, in the closed position the jaws (51, 56) are parallel and spaced apart from one another to receive the cartridge (90). The follower (62) is positioned at the beginning of the second profile (58B) which prevents the upper jaws (56) from opening, thus locking the jaws (51, 56) in their closed position. The cartridge (90) is slid proximally between the jaws (51, 56). The tooth (59) engages with the step (99) once the cartridge (90) is fully inserted to latch the cartridge (90) into the receiver (50).

Figure 6C:
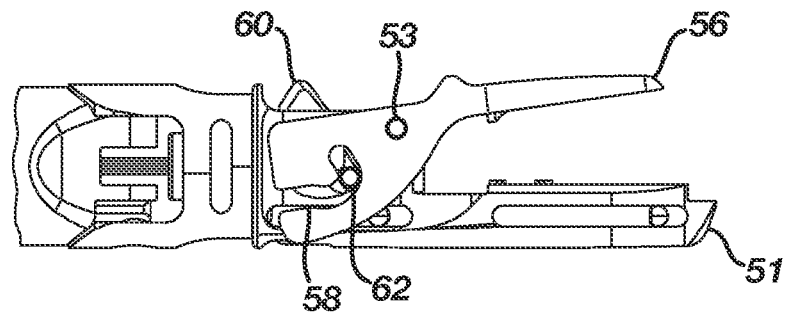
FIG. 6C depicts a side view of a receiver in its partially opened position.

The cartridge (90) is released from the receiver (50) by opening the jaws (51, 56). As shown in FIG. 6C, proximal movement of the button (60) will advance the follower (62) through the second profile (58B) thus pivoting the upper jaw (56) about the pin (53) and moving the upper jaw (56) to its partially opened position. The button (60) is biased distally by spring (64), so when the button (60) is released the follower (62) will reverse through the second profile (58B) and close the upper jaw (56). Thus, in the partially opened position, the upper jaw (56) is biased closed by the spring (64).

Figure 6D:
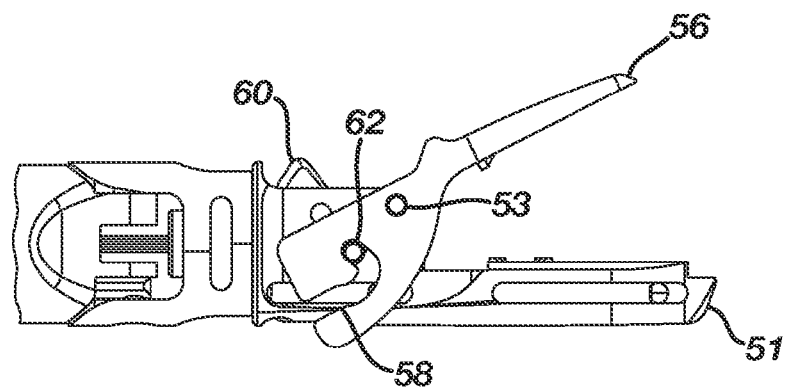
FIG. 6D depicts a side view of a receiver in its fully opened position.

As shown in FIG. 6D, the jaws (51, 56) can be moved to their fully opened position by pulling the upper jaw (56) upward away from the lower jaw (51). The follower (62) will advance through the third profile (58C) which prevents the button (60) from pivoting and prevents the spring (64) from moving the button (60) distally, so the button (60) remains in its proximal position. Thus, the upper jaw (56) will remain in the fully opened position until the upper jaw (56) is pushed downward and the follower (62) returns to the second profile (58B). Among other advantages, the fully opened upper jaw (56) facilitates cleaning of the receiver (50).

Figure 7:
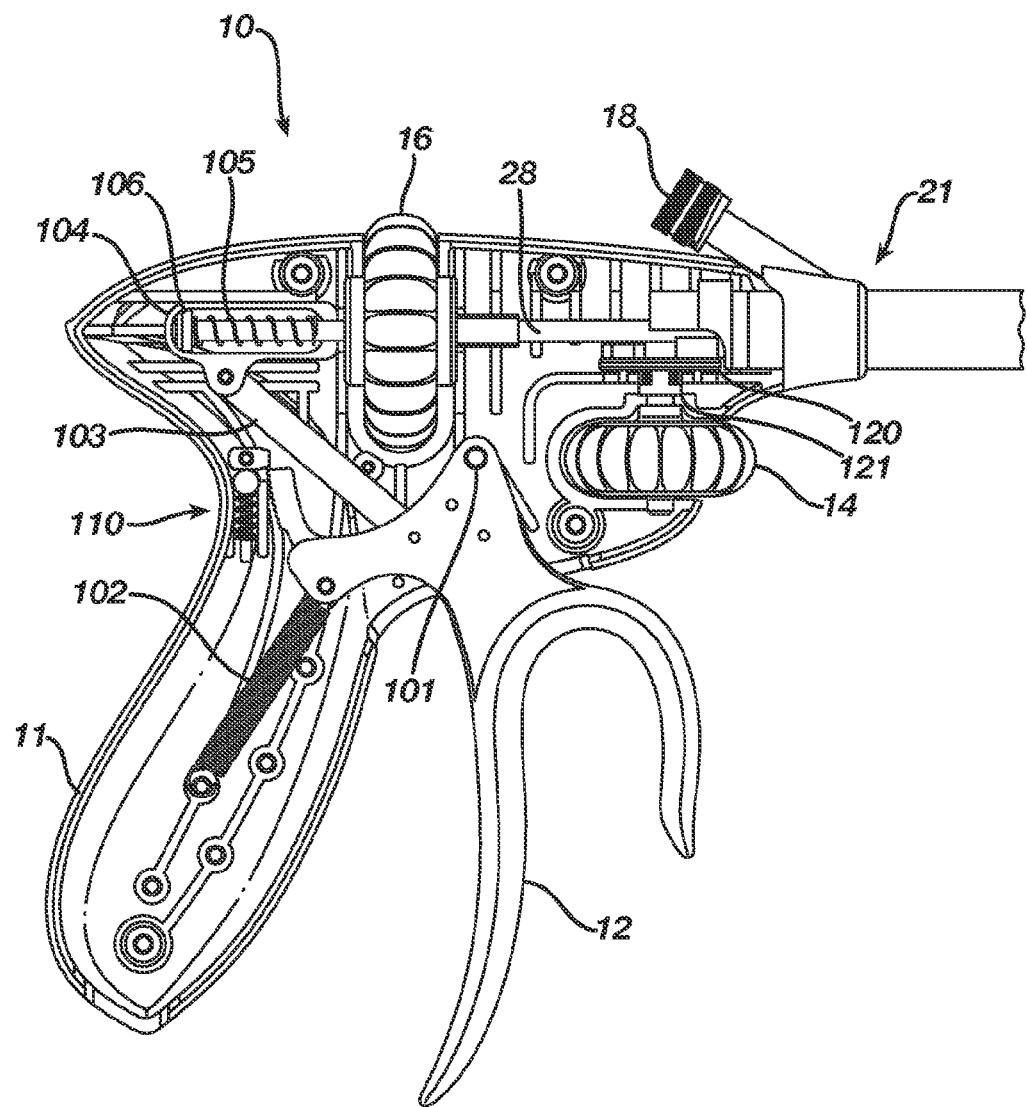
FIG. 7 depicts a side view of a handle actuator.

FIG. 7 illustrates an embodiment of a manual actuator (10). The trigger (12) pivots about the pin (101) between an opened position (as shown here) and closed position towards the shroud (11). One pump of the trigger (12) from the opened to closed positions actuates needle driver (86) through its drive stroke. Moving the trigger (12) from the closed to opened positions actuates the needle driver (86) through its return stroke. The spring (102) biases the trigger (12) to its opened position. One end of the link (103) is connected to the trigger (12) intermediate the pivot (101) and spring (102). The link (103) is connected at the other end to a sled (104). In this embodiment the sled (104) is generally aligned with the drive rod (28) and slides longitudinally in the shroud (11) when the trigger (12) is actuated. A spring (105) is interposed between the sled (104) and a flange (106) on the drive rod (28). In this embodiment, the spring (105) is coaxially arranged around the driver rod (28) and is compressed between the flange (106) and the sled (106). The spring (105) may be pre-loaded with a compressive force.

Closing the trigger (12) will drive the sled (104) proximally, thus compressing the spring (105) against the flange (106) to impart a proximal force on the drive rod. The spring (105) acts to limit the force that may be transmitted to the needle applier (30). If the resistive load experienced by the needle applier (30) exceeds the compressive force of the spring (105), then the spring (105) would compress further without deflecting the flange (106). For instance, if the surgeon attempts to pass needle (70) through hard tissue, such as bone, the spring (105) would deflect and prevent undue loads being transmitted through the drive rod (28) that could otherwise damage the needle applier (30) or bend the needle (70).

The rotary knob (16) is operable to selectively rotate the circular needle applier (30) about the bearing (24). The drive rod (28) includes an axially sliding spline interface with the rotary knob (16) providing torsional engagement while allowing relative longitudinal translation. Thus, turning the rotary knob (16) will rotate the drive rod (28) which in turn rotates the receiver (50) about the bearing (24).

The ratchet mechanism (110) prevents the trigger (12) from moving in the open direction until the needle driver (86) has been actuated through the full drive stroke. Optionally, the ratchet mechanism (110) may be bi-directional to prevent the trigger (12) from moving in the close direction until the needle driver (86) has been actuated through the full return stroke.

FIGS. 8A-D illustrate an example of a bi-directional ratchet mechanism (110) comprising the rack (111) having a first end (111A), a second end (111B), and the length extending between the first and second ends. The rack (111) is connected to the trigger (12) and may have a plurality of teeth (112) along the length; however, toothless frictional racks may also be used to avoid backlash or provide quieter action. A pawl (115) pivots about the pin (116). The spring (113) acts on the ball (114) to bias the pawl (115) to a reset position generally normal to the rack (111). The pawl has two edges (115A, B) adapted to engage the teeth (112).

Figure 8A:
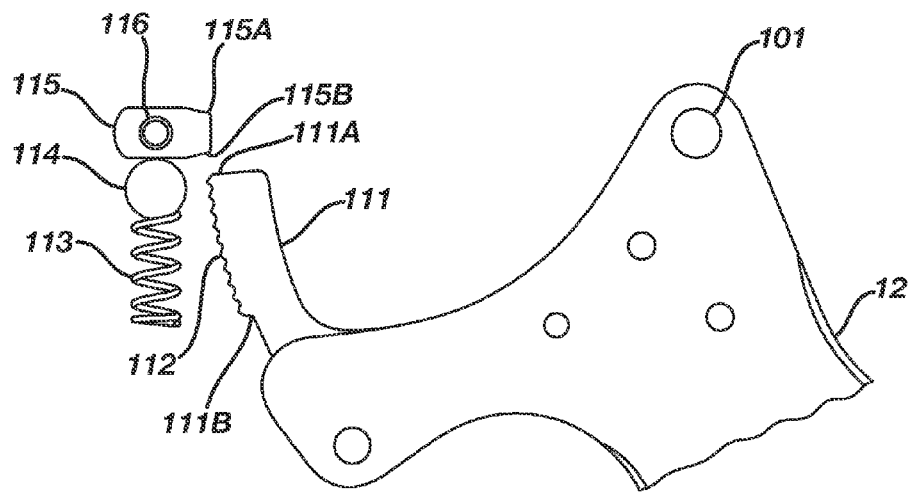
FIG. 8A depicts a ratchet mechanism.
Figure 8B:
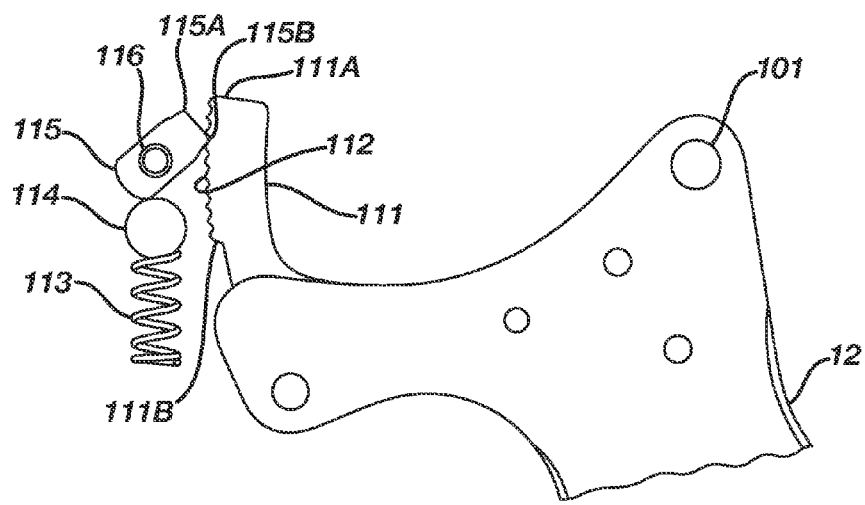
FIG. 8B depicts a ratchet mechanism.
Figure 8C:
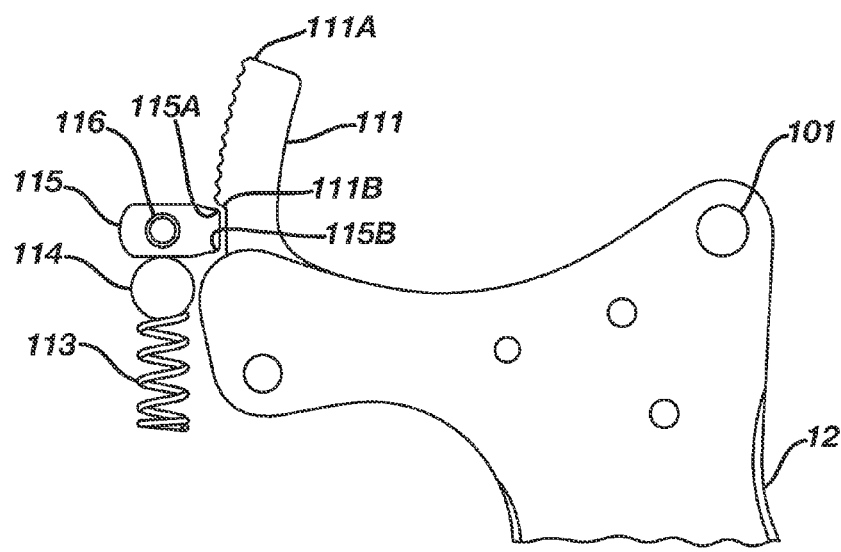
FIG. 8C depicts a ratchet mechanism.
Figure 8D:
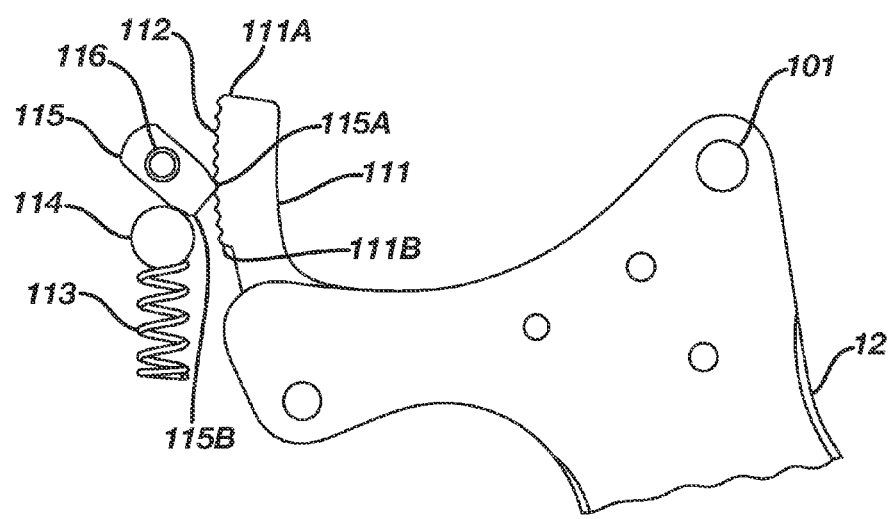
FIG. 8D depicts a ratchet mechanism.

As shown in FIG. 8A, when the trigger (12) is in the open position the pawl (15) is positioned beyond the first end (111A) of the rack (111) and the spring (113) biases the pawl (115) to its reset position. As shown in FIG. 8B, upon partially closing the trigger (112) the rack (111) moves and pivots pawl (115) to a first trailing oblique angle relative the rack (111). In this position the edge (115B) of the pawl (115) engages the teeth (112) preventing the trigger (12) from opening. As shown in FIG. 8C, upon fully closing the trigger (112) the pawl (111) is positioned beyond the second end (111B) of the rack (111) and the spring (113) biases the pawl (115) to its reset position. Once the pawl (115) is reset, the trigger (12) can now move in the opposite direction. As shown in FIG. 8D, upon partially opening the trigger (12) the rack (111) moves and pivots the pawl (115) to a second trailing oblique angle relative the rack (111). In this position the edge (115A) of the pawl (115) engages the teeth (112) preventing the trigger (12) from closing. Upon fully opening the trigger (112) the pawl (111) is positioned beyond the first end (111A) of the rack (111) and the spring (113) biases the pawl (115) to its reset position, as shown in FIG. 8A.

The length of the rack (111) may be calibrated such that the pawl (115) will not reset while closing and opening of the trigger (12) until the needle driver (86) has been actuated through its full drive and return strokes, respectively. This feature is beneficial in that it prevents partial actuation of the circular needle applier (30) and improves the surgeon's awareness about the angular location of the needle (70) in the track (84).

Figure 9:
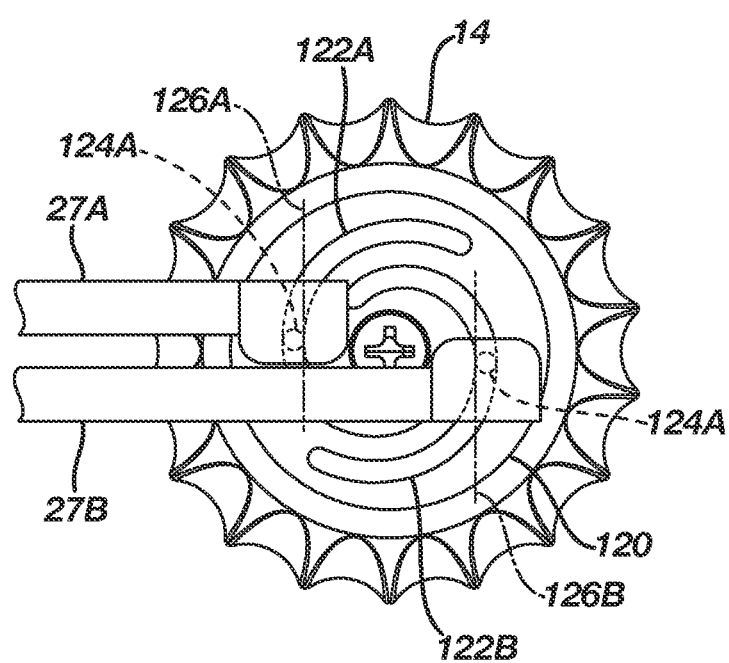
FIG. 9 depicts a top view of an articulation control.

The rotary knob (14) is operable to selectively articulate the joint (23). The rotary knob (14) rotates in a plane spaced below and generally parallel with the shaft (20). An axle (121) connects the rotary knob (14) to a disk (120) in the shroud (11) that also rotates in a plane generally parallel with the shaft (20). As shown in FIG. 9, the disk (120) comprises first and second cam slots (122A, B) each having a length with an angular and radial components. In this embodiment, the cam slots (122A, B) are two identical spirals offset 180 degrees from one another. Each cam slot (122A, B) has an angular span between about 220 degrees and about 300 degrees, with their angular spans overlapping one another. The cam slots (122A, B) also increase their distance from the center in of the disk (120) in the same angular direction. Each cam slot (122A, B) has a radial span of about 0.100 inches and about 0.155 inches. Naturally, the configuration and dimensions of the cam slots may also differ from the foregoing.

The cam slot (122A) receives the cam follower (124A) on the distal half of the disk (120), and cam slot (122B) receives the cam follower (124B) on the proximal half of the disk (120). The followers (124A, B) extend downward and generally normal from the rods (27A, B), respectively. In this embodiment, the followers (124A, B) are medially offset from longitudinal axes of the respective drive rod (27A, B). Rods (27A, B) are constrained to slide axially, so clockwise rotation of the disk (120) moves the rod (27B) distally and moves rod (27A) proximally, thereby articulating the joint (23) to the right. Similarly, counterclockwise rotation of the disk (120) moves the rod (27B) proximally and moves the rod (27A) distally to articulate the joint (23) to the left.

The cam slots (122A, B) each comprise a tangent axis (126A, B) where the cam slots (122A, B) is engaged by the respective cam followers (124A, B). The tangent axes (126A, B) may be substantially normal to the longitudinal axes of the rods (27A, B) so axial push and pull loads on the rods (27A, B) introduced by side loads on the receiver (50) will not cause the disk (120) to rotate. Accordingly, the joint (23) will remain locked at its articulated angle. Frictional interfaces or detents may be added to further prevent unintentional articulation, such as between the followers (124A, B) and the cam slots (122A, B), between the disk (120) and the shroud (11), between the axle (121) and the shroud (11), and the like.

Figure 10:
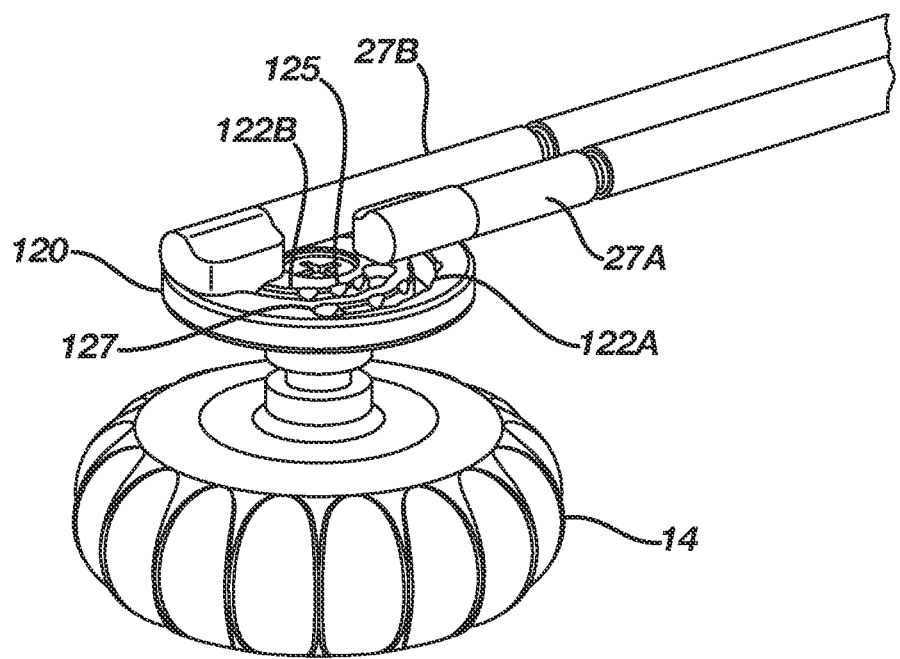
FIG. 10 depicts a perspective view of an articulation control.

FIG. 10 illustrates an alternative embodiment of an articulation control. A plurality of detents (125) are positioned along the cam slots (122A, B). In addition to preventing unintentional articulation, the detents (125) may provide feedback to the surgeon indicating various angular positions of the circular needle applier (30) relative the elongate shaft (20). The detents (125) may be indexed to correspond to one or more predetermined articulation angles, such as 0 degrees, 15 degrees, 45 degrees, and the like, or the detents (125) may be equally distributed along the cam slots (122A, B). Larger detents (127) may be located at the ends of the cam slots (122A, B).

Figure 11:
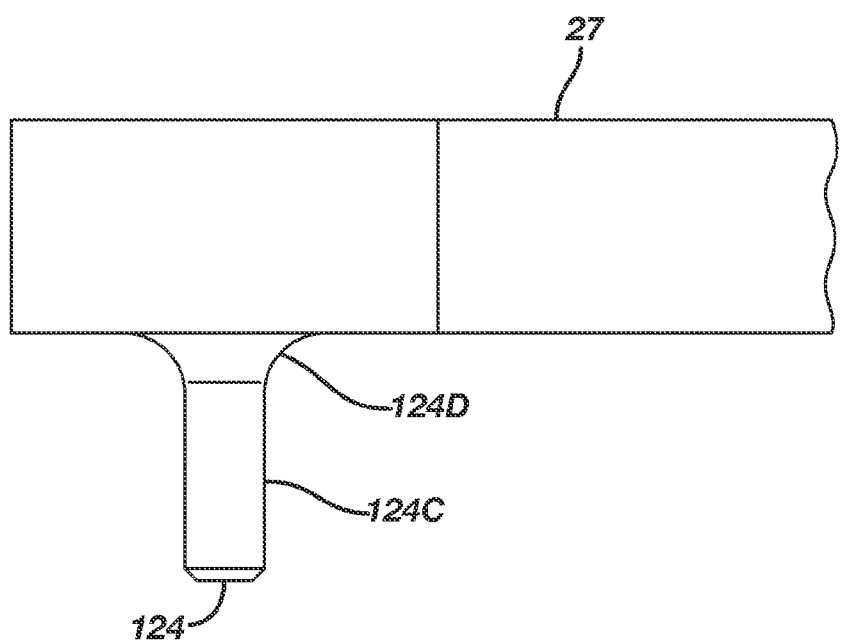
FIG. 11 depicts a side view of an articulation rod and follower.

The detents (125) open to the top surface of the disk (120), but only partially extend into the cam slots (122A, B). As shown in FIG. 11, the follower (124) extends downward from the articulation rod (27). The follower (124) includes a straight portion (124C) that closely fits in the cam slots (122A, B) and a radius portion (124D) dimensioned to be received by the detents (125). As the disk (120) rotates, the radius portion (124D) will raise and lower into the detents (125) but the straight portion (124C) will follow and remain engaged in the cam slots (122A, B). Preferably, the rod (27) will be biased downward towards the disk (120) to provide a tactile and/or audible "click" as the radius portion (124D) engages the detents (125).

Having shown and described various embodiments and examples of the present invention, further adaptations of the methods and devices described herein can be accomplished by appropriate modifications by one of ordinary skill in the art without departing from the scope of the present invention. Several of such potential modifications have been mentioned, and others will be apparent to those skilled in the art. For instance, the specific materials, dimensions, and the scale of drawings will be understood to be non-limiting examples. Accordingly, the scope of the present invention should be considered in terms of the following claims and is understood not to be limited to the details of structure, materials, or acts shown and described in the specification and drawings.

The invention claimed is:

1. A surgical suturing device, comprising:
a cartridge having a needle and suture;
an elongate shaft having a proximal end and a distal end;
an actuator connected to the proximal end of the elongate shaft;
a receiver connected to the distal end of the elongate shaft, the receiver comprising a stationary jaw and a pivoting jaw having a closed position adapted to receive and retain the cartridge and an opened position adapted to release the cartridge, a spring biasing the pivoting jaw towards the closed position, the pivoting jaw having a second opened position spaced further from the stationary jaw than in the opened position, wherein in the second opened position the spring does not bias the pivoting jaw towards the closed position.

2. The surgical suturing device of claim 1, wherein the stationary jaw comprises a rotary drive and the cartridge comprises a rotary input adapted to engage the rotary drive.

3. The surgical suturing device of claim 1, wherein the stationary jaw comprises two longitudinal rails dimensioned and adapted to receive the cartridge and laterally retain the cartridge.

4. The surgical suturing device of claim 1, wherein the pivoting jaw comprises a resiliently biased tooth oriented toward the stationary jaw, the tooth being dimensioned and adapted to engage and distally retain the cartridge.

5. The surgical suturing device of claim 1, further comprising a button operative to move the jaws from the closed position to the opened position.

6. The surgical suturing device of claim 5, wherein the button is positioned adjacent the jaws.

7. The surgical suturing device of claim 5, further comprising a follower connected to the button, the follower moves in a cam slot, and wherein actuation of the button drives the follower along the cam slot to open and close the jaws.

8. The surgical suturing device of claim 7, further comprising a spring acting on the button and biasing the jaws closed.

9. The surgical suturing device of claim 1, wherein the actuator comprises a handle.

10. A surgical suturing device, comprising:
a cartridge comprising a needle and suture;
an elongate shaft having a proximal end and a distal end;
an actuator connected to the proximal end of the elongate shaft;
a pair of jaws connected to the distal end of the elongate shaft, the jaws having a closed position adapted to receive and retain the cartridge, and wherein the jaws are latched in the closed position;
a partially opened position adapted to release the cartridge wherein the jaws are biased by a spring from the first opened position towards the closed position; and
a fully opened position spaced apart further than the partially opened position, wherein spring does not bias the jaws towards the closed position.

11. The surgical suturing device of claim 10, further comprising a button adjacent the jaws operable to unlatch the jaws from the closed position.

12. The surgical suturing device of claim 11, wherein the jaws comprise a stationary jaw and a pivoting jaw that pivots about an axis.

13. The surgical suturing device of claim 12, further comprising a cam slot on the pivoting jaw and a follower on the button, the follower moves in the cam slot between a first position, a second position, and a third position, the cam slot having a first cam profile between the first and second positions and a second cam profile between the second and third positions;
wherein in the first position the follower engages the cam slot so as to prevent the jaws from opening thereby latching the jaws in the closed position;

actuation of the button moves the follower along the first cam profile to unlatch the jaws and to move the jaws to the first opened position; and the second cam profile is substantially equidistant from the axis.

* * * * *